United States Patent [19]

Tuli et al.

[11] Patent Number: 5,916,850
[45] Date of Patent: Jun. 29, 1999

[54] MULTIFUNCTIONAL ADDITIVES FROM CASHEW NUT SHELL LIQUID

[75] Inventors: Deepak Kumar Tuli; Rakesh Sarin; Madan Mohan Rai; Akhilesh Kumar Bhatnagar, all of Faridabad, India

[73] Assignee: Indian Oil Corporaton Limited, Mumbai, India

[21] Appl. No.: 08/965,147

[22] Filed: Nov. 6, 1997

[51] Int. Cl.$^6$ .................................................. C10M 137/08
[52] U.S. Cl. .......................... 508/353; 508/429; 508/436; 558/112
[58] Field of Search ..................... 508/436, 429, 508/353; 558/112

[56] References Cited

U.S. PATENT DOCUMENTS

| | | | |
|---|---|---|---|
| 2,411,160 | 11/1946 | Hughes | 508/353 |
| 3,361,856 | 1/1968 | Le Suer | 508/429 |
| 3,755,250 | 8/1973 | Wollensak et al. | 508/429 |
| 4,328,113 | 5/1982 | Horodysky et al. | 252/49.6 |
| 4,395,498 | 7/1983 | Benham | 523/158 |
| 4,478,732 | 10/1984 | Horodysky et al. | 252/49.6 |
| 4,505,830 | 3/1985 | Vinci | 252/33 |
| 4,618,437 | 10/1986 | Horodysky | 252/32.5 |
| 4,705,879 | 11/1987 | Dressler | 508/429 |
| 4,721,802 | 1/1988 | Forsberg | 508/436 |
| 5,218,038 | 6/1993 | Johnson et al. | 524/541 |
| 5,354,484 | 10/1994 | Schwind et al. | 508/436 |
| 5,433,774 | 7/1995 | Kapl et al. | 106/36 |

*Primary Examiner*—Jerry D. Johnson
*Attorney, Agent, or Firm*—Venable; George H. Spencer; Ashley J. Wells

[57] ABSTRACT

A process for the preparation of amino di(alkylaryl) phosphorodithioate for use as an additive in a lubricant composition so as to impart improved coefficient of friction, wear reduction, antioxidant and extreme pressure properties, including the steps of (a) reacting a starting material selected from the group consisting of distilled cashew nut shell liquid and distilled hydrogenated cashew nut shell liquid with phosphorus pentasulfide to obtain unpolymerized cashew nut shell liquid phosphorodithioic acid, the reacting being carried out at a temperature ranging from 40 to 80° C. when the starting material is distilled cashew nut shell liquid and at a temperature ranging up to 140° C. and above when the starting material is distilled hydrogenated cashew nut shell liquid; and (b) condensing the unpolymerized cashew nut shell liquid phosphorodithioic acid with at least one amine to obtain the amino di(alkylaryl) phosphorodithioate. A lubricant containing a major proportion of a material selected from the group consisting of an oil of lubricating viscosity and a grease; and remainder an additive including amino di(alkylaryl)phosphorodithioate prepared by the foregoing process.

17 Claims, No Drawings

MULTIFUNCTIONAL ADDITIVES FROM CASHEW NUT SHELL LIQUID

BACKGROUND OF THE INVENTION

1. Field of the Invention

This invention relates to the preparation of multifunctional additives from cashew nut shell liquid.

2. Description of the Related Art

This invention relates to a process for the preparation of amino di(alkylaryl)phosphorodithioates, from naturally occurring, biodegradable, vegetable based cashew nut shell liquid, for use in a lubricant, so as to impart suitable properties of friction reducing, antioxidant, antiwear and extreme pressure additives.

Cashewnut shell liquid (CNSL) occurs as a reddish brown viscous liquid in the soft honeycomb structure of the shell of cashewnut, a plantation product obtained from the cashew tree, *Anacardium Occidentale L*. Native to Brazil, the tree grows in the coastal areas of Asia & Africa. Cashewnut attached to cashew apple is grey colored, kidney shaped and 2.5–4 cm long. The shell is about 0.3 cm thick, having a soft leathery outer skin and a thin hard inner skin. Between these skins is the honeycomb structure containing the phenolic material popularly called CNSL. Inside the shell is the kernel wrapped in a thin brown skin, known as the testa.

The nut thus consists of the kernel (20–25%), the shell liquid (20–25%) and the testa (2%), the rest being the shell. CNSL, extracted with low boiling petroleum ether, contains about 90% anacardic acid and about 10% cardol. CNSL, on distillation, gives the pale yellow phenolic derivatives, which are a mixture of biodegradable unsaturated m-alkylphenols, including cardanol. Catalytic hydrogenation of these phenols gives a white waxy material, predominantly rich in tetrahydroanacardol.

CNSL and its derivatives have been known for producing high temperature phenolic resins and friction elements, as exemplified in U.S. Pat. Nos. 4,395,498 and 5,218,038. Friction lining production from CNSL is also reported in U.S. Pat. No. 5,433,774. Likewise, it is also known to form different types of friction materials, mainly for use in brake lining system of automobiles and coating resins from CNSL.

Friction is also a problem any time two surfaces are in sliding or rubbing contact. It is of special significance in an internal combustion engine and related power train components, because loss of a substantial amount of the theoretical mileage from a gallon of fuel is traceable directly to friction.

It is also known that sliding or rubbing metal or other solid surfaces are subject to wear under conditions of extreme pressure. Wear is particularly acute in modern engines in which high temperatures and contact pressures are prevalent. Under such conditions, severe erosion of metal surfaces can take place even with present generation lubricants unless a load carrying or antiwear additive is present therein. These load carrying, friction reducing, antiwear and antioxidant additives are generally organic compounds, having polar groups, which are capable of forming a film at the mating metal surfaces.

Considerable work has been reported with lubricating oils, mineral and synthetic, to enhance their antioxidant, antiwear and friction reducing properties, by modifying them with suitable additives. The use of lubricant additives containing phosphorus and sulfur has been well documented and widely implemented commercially. These include acid phosphates, thiophosphates, phosphites, phosphate ester, metal dithiophosphates, metal dithiocarbamates, xanthates, phosphonates and the like. Amine compositions have also found wide use as friction reducing additives as exemplified by U.S. Pat. No. 4,328,113 which relates to alkyl amines and diamines and borated adducts of alkylamine and diamines. U.S. Pat. 4,478,732 describes imidazoline salts of acid phosphates, while U.S. Pat. 4,505,830 is drawn to C10–C20 alkyl substituted imidazoline salts of boric acid or phosphoric acid as useful in metal working lubricants. U.S. Pat. 4,618,437 describes boronated internal imidazoline acid phosphates as effective friction reducers.

The present invention relates to lubricant compositions and more particularly, to lubricant compositions comprising oils of lubricating viscosity or greases thereof containing a minor friction reducing, antiwear and antioxidant additive of hydrocarbyl amine salt of di(alkylaryl)phosphorodithioic acid derived from cashew nut shell liquid.

An object of this invention is to propose a process for the preparation of various amine salts of di(alkylaryl) phosphorodithioic acids, derived from cashew nut shell liquid, which when blended into lubricants, provide effective multifunctional friction reducing, antioxidant, antiwear and extreme pressure activities.

SUMMARY OF THE INVENTION

According to this invention, there is provided a process for the preparation of amino di(alkylaryl)phosphorodithioate for use as an additive in a lubricant composition, comprising in the steps of:

a) reacting distilled CNSL or hydrogenated distilled CNSL with phosphorus pentasulfide, to obtain CNSL phosphorodithioic acid;

b) subjecting said CNSL phosphorodithioic acid to the step of condensation with amines to obtain said amino di(alkylaryl)phosphorodithioate.

Further according to this invention, there is provided a lubricant comprising of a major portion of an oil of lubricating viscosity or grease and the remainder being an additive comprising of amino di(alkylaryl) phosphorodithioate, derived from distilled CNSL.

DESCRIPTION OF THE PREFERRED EMBODIMENTS

The present invention describes a process for preparation of novel multifunctional additives, for use in lubricants and fuels. These additives are prepared by the reaction of di(alkylaryl)phosphorodithioic acids, derived from cashew nut shell liquid with various amines. This invention is more particularly directed to lubricant compositions containing minor additive concentrations of primary, secondary or tertiary amine adducts of di(alkylaryl)phosphorodithioic acids, derived from distilled cashew nut shell liquid, and a major amount of oil of proper lubricating viscosity, which exhibit excellent antiwear, extreme pressure, antifriction and antioxidant properties. Concentrations as little as 1% in fully formulated synthetic and mineral oil based formulations reduce the coefficient of friction by approximately 50% and thus improve lubricity. Synergistic wear reduction is seen to the extent of 60–65%, due to the modest phosphorus content of the highly surface active additive. Antioxidant properties are seen as expected, to the level of 30–40%. The increase in extreme pressure properties of 50–70% over the base fluid are also obtained.

Accordingly, this invention is specifically directed to lubricant compositions comprising a major proportion of an oil of lubricating viscosity or grease prepared therefrom and a minor effective proportion of a friction reducing/antiwear/extreme pressure/antioxidant additive selected from the group consisting essentially of a primary amine, secondary amine or tertiary amine salt of the di(alkylaryl) phosphorodithioic acids, prepared from distilled CNSL or hydrogenated distilled CNSL, wherein the primary amine, secondary amine or tertiary amine salt of the di(alkylaryl) phosphorodithioic acids are prepared from the condensation reaction of said phosphorodithioic acids with said amines or mixtures of said primary, secondary or tertiary amines.

The amines useful in this invention include primary amines, secondary amines and tertiary amines. Preferred are secondary amines such as dipentylamine, dihexylamine, dicyclohexylamine, bis(2-ethylhexyl)amine, dioctylamine, dinonylamine, didodecylamine, and primary amines such as oleyl amine, stearyl amine, isostearyl amine, cocoamine, tallow amine, hydrogenated tallow amine, t-alkylamines, diethanolamine, dodecylamine, decylamine, octylamine, 2-ethylhexylamine and butylamine; and tertiary amines such as triethylamine, tributylamine, triethanol amine. Suitable diamines include diethylenetriamine, triethylenetetramine, N-coco-1,3-propylenediamine, N-oleyl-1.3-propylene diamine. Generally amines having at least 2 to 4 and up to 24 to 26 carbon atoms including mixtures of such amines have been found to be highly useful in this invention.

All the reactants used in the process in accordance with this invention can be obtained commercially or made by any convenient means known to the art.

Generally speaking, the process of manufacturing the additives in accordance with this invention may be carried out as follows:

Specifically, cashew nut shell liquid or hydrogenated cashew nut shell liquid, is distilled at reduced pressure to yield a mixture of biodegradable alkylated phenols. Such a mixture is converted to their corresponding phosphorodithioic acids by reaction with phosphorus pentasulfide and the phosphorodithioic acids are then converted to form the amine salts thereof by reacting with suitable hydrocarbyl amines, diamines or triamines or mixtures thereof. Solvents can optionally be used in either step of the reaction. A wide temperature range can be used to perform either reaction from as low as room temperature to as high as 140° C. or more, with 40–80° C., often preferred. Preferably, the amine and the phosphorodithioic acid are reacted in stoichiometric ratios of acid to amine of from about 3:1 to about 1:3, preferably from 2:1 to 1:2. An excess of amine can be used in this step or a small amount of free acidity can be left by undercharging the amine or the mixtures of amines.

The lubricants contemplated for use herein include both mineral and synthetic hydrocarbon oils of lubricating viscosity, mixtures of mineral and synthetic oils and greases prepared therefrom. Typical synthetic oils are: polypropylene glycol, trimethylol propane esters, neopentyl and pentaerythritol esters, polyethylene glycol, di(2-ethylhexyl) adipate, fluorocarbons, siloxanes, phenoxy phenyl ethers and poly alphaolefms.

The amount of additive in the lubricant compositions may range from about 0.1 to about 10% by weight of the total lubricant composition. Preferred is from 0.5 to 5 wt %. Other additives which may be present include polyalkyl succinimide and polyalkenyl ester dispersants, metallic (calcium or magnesium) sulfonates or phenates, metallic phosphorodithioates, polymeric viscosity index improvers and other additives used in lubricants.

The following examples illustrate the invention, but without intending to imply any limitation thereon.

EXAMPLE 1

Preparation of CNSL phosphorodithioic acid

Approximately 300 g of distilled cashew nut shell liquid was charged to a 1 litre reactor equipped with agitator and condenser. The contents were warmed to 50° C. Subsequently 222 g of phosphorus pentasulfide was slowly added to the reactor under constant stirring, over a period of one hour, while maintaining temperature of 50–70° C. After addition, the temperature was further maintained at 90–100° C. for three hours. On completion of reaction, the product was filtered.

EXAMPLE 2

Bis(2-ethylhexyl)amine Salt of CNSL phosphorodithioic acid

Approximately 1.0 mole of product of example 1 was treated with 1.0 mole of bis(2-ethylhexyl)amine for 20–40 minutes at 30–40° C., with continuous stirring, till the exothermic reaction was complete, leading to the formation of bis(2-ethylhexyl)amine salt of CNSL phosphorodithioic acid.

EXAMPLE 3

Dipentylamine Salt of CNSL phosphorodithioic acid

Approximately 1.0 mole of product of example 1 was treated with 1.0 mole of dipentylamine for 20–40 minutes at 30–40° C., with continuous stirring, till the exothermic reaction was complete, leading to the formation of bis(2-ethylhexyl)amine salt of CNSL phosphorodithioic acid.

EXAMPLE 4

Primene-JMT amine salt of CNSL phosphorodithioic acid

Approximately 1.0 mole of product of example 1 was treated with 1.0 mole of commercial t-alkyl primary amine ($C_{18}$), Primene-JMT, for 20–40 minutes at 30–40° C., with continuous stirring, till the reaction was complete, leading to the formation of t-alkyl primary amine (Primene-JMT) salt of CNSL phosphorodithioic acid.

EXAMPLE 5

Primene-81R amine salt of CNSL phosphorodithioic acid

Approximately 1.0 mole of product of example 1 was treated with 1.0 mole of a commercial t-alkyl primary amine ($C_{12}$), Primene-81R, for 20–40 minutes at 30–40° C., with continuous stirring, till the exothermic reaction was complete, leading to the formation of t-alkyl primary amine (Primene-81R) salt of CNSL phosphorodithioic acid.

EXAMPLE 6

Tributylamine salt of CNSL phosphorodithioic acid

Approximately 1.0 mole of product of example 1 was treated with 1.0 mole of tributylamine, for 20–40 minutes at 30–40° C., with continuous stirring, till the exothermic reaction was complete, leading to the formation of tributylamine salt of CNSL phosphorodithioic acid.

EXAMPLE 7

Triethanolamine salt of CNSL phosphorodithioic acid

Approximately 1.0 mole of product of example 1 was treated with 1.0 mole of triethanolamine, for 20–40 minutes at 30–40° C., with continuous stirring, till the exothermic reaction was complete, leading to the formation of triethanolamine salt of CNSL phosphorodithioic acid.

EXAMPLE 8

2-Ethylhexylamine & Bis(2-ethylhexyl)amine salt of CNSL phosphorodithioic acid.

Approximately 1.0 mole of product of example 1 was treated with a mixture of 0.5 mole of 2-ethylhexylamine and 0.5 mole of bis(2-ethylhexyl)amine, for 20–40 minutes at 30–40° C., with continuous stirring, till the exothermic reaction was complete, leading to the formation of 2-ethylhexylamine & bis(2-ethylhexyl)amine salt of CNSL phosphorodithioic acid.

Performance evaluation of products

The synthesised alkylarylaminophosphorodithioates were evaluated in a solvent refined, highly paraffinic, 150 neutral grade, mineral base oil having a kinematic viscosity of 28.8 at 40° C. and 5.0 cSt at 100° C.

A four ball machine was used for studying antiwear properties, involving measurement of wear scar on the ball at 196N load, 55° C. temperature and 1800 rpm for one hour. In general, alkylarylaminophosphorodithioates reduced wear scar over unformulated base oil, by 55–65% at 0.5% dosage (Table-1).

Extreme pressure properties were determined by measuring the weld load, in duplicate, on a four ball machine according to ASTM D-2783 test method, while increasing the load in stages of 981N, 1099N, 1236N, 1570N, 1766N, 1962N and 2206N. Synthesised alkylarylaminophosphorodithioates showed an increase in weld load from 40–80% at additive dosage of 0.5–2.0% (Table-1).

Antioxidant performance of the blends was determined by differential scanning calorimetry (DSC), adopting temperature range of 100–350° C., heating rate of 10° C. per minute and oxygen flow rate of 60–80 ml/minute. The temperature at the onset of oxidation was taken as the criterion for assessment of antioxidant performance. In general, claimed alkylarylaminophosphorodithioates increased the temperature of the onset of oxidation by 30–85° C., w.r.t. unformulated base oil (Table-1).

Antifriction properties were measured by an oscillating friction and wear test apparatus, under the point contact conditions. The minimum stabilised value of the coefficient of the friction, recorded during the continuous run, was taken as a criterion for friction. Synthesised alkylarylaminophosphorodithioates, at 0.5–1.0% level, reduced coefficient of friction by 35–55%, as compared to base oil (Table-1).

The above data clearly demonstrates that additive amounts of the di(alkylaryl)aminophosphorodithioates, derived from CNSL, in premium quality automotive and industrial lubricants significantly enhance the lubricant's energy efficiency, antiwear, antioxidant and extreme pressure properties. The unique additives described in this patent application are useful at low concentrations, are non-metallic and do not contain any potentially corrosive sulfur. These salts can be readily prepared in a one pot process. Furthermore, development and use of these multifunctional lubricant/fuel additives, derived from CNSL, a renewable and biodegradable product from vegetable sources and often available at very low price, would amount to substantial overall reduction in the cost of quality, energy efficient lubricant/fuel formulations.

TABLE 1

PERFORMANCE EVALUATION OF CNSL DERIVED MULTIFUNCTIONAL ADDITIVES

| EX-AMPLE No. | ADDITIVE CONC. (% w/w) | COEFF. OF FRICTION ($\mu$) | WEAR SCAR DIA (mm) | WELD LOAD (Kg) | ON-SET OF OXIDATION TEMPERATURE (° C.) |
|---|---|---|---|---|---|
| 2 | 0.5 | 0.10 | 0.40 | 180 | 229.8 |
| 2 | 1.0 | 0.09 | 0.35 | 180 | 235.7 |
| 3 | 0.5 | 0.105 | 0.40 | 180 | 274.5 |
| 3 | 1.0 | 0.08 | 0.35 | 200 | 279.2 |
| 4 | 0.5 | 0.095 | 0.45 | 180 | 255.3 |
| 4 | 1.0 | 0.08 | 0.40 | 180 | 265.1 |
| 5 | 0.5 | 0.095 | 0.45 | 160 | 229.4 |
| 5 | 1.0 | 0.085 | 0.35 | 180 | 236.9 |
| 6 | 0.5 | 0.10 | 0.45 | 180 | 241.4 |
| 6 | 1.0 | 0.095 | 0.40 | 200 | 253.4 |
| 7 | 0.5 | 0.095 | 0.40 | 160 | 236.5 |
| 7 | 1.0 | 0.08 | 0.35 | 180 | 242.2 |
| 8 | 0.5 | 0.09 | 0.35 | 180 | 246.3 |
| 8 | 1.0 | 0.085 | 0.35 | 180 | 256.5 |
| BASE OIL | — | 0.17 | 1.00 | 112 | 196.7 |

We claim:

1. A process for the preparation of amino di(alkylaryl) phosphorodithioate for use as an additive in a lubricant composition so as to impart improved coefficient of friction, wear reduction, antioxidant and extreme pressure properties, comprising the steps of:
   (a) reacting a starting material selected from the group consisting of distilled cashew nut shell liquid and distilled hydrogenated cashew nut shell liquid with phosphorus pentasulfide to obtain unpolymerized cashew nut shell liquid phosphorodithioic acid, the reacting being carried out at a temperature ranging from 40 to 80° C. when the starting material is distilled cashew nut shell liquid; and
   (b) condensing the unpolymerized cashew nut shell liquid phosphorodithioic acid with at least one amine to obtain the amino di(alkylaryl) phosphorodithioate.

2. The process as claimed in claim 1, wherein the at least one amine is selected from the group consisting of primary, secondary and tertiary alkyl/alkylaryl amines having an alkyl chain ranging from $C_1$ to $C_{20}$.

3. The process as claimed in claim 1, wherein the at least one amine is a mixture of amines selected from the group consisting of primary, secondary and tertiary alkyl and alkylaryl amines and alkylaryl amines having an alkyl chain ranging from $C_1$ to $C_{20}$.

4. The process as claimed in claim 1, wherein the reacting and the condensing are carried out in the presence of a solvent.

5. The process as claimed in claim 1, wherein the distilled cashew nut shell liquid comprises hydrogenated distilled cashew nut shell liquid.

6. The process as claimed in claim 1, wherein the at least one amine and the phosphorodithioic acid are present in stoichiometric ratios of acid to amine ranging from about 3:1 to about 1:3.

7. The process as claimed in claim 1, wherein the at least one amine and the phosphorodithioic acid are present in stoichiometric ratios of acid to amine ranging from 2:1 to 1:2.

8. A lubricant, comprising:
   a major proportion of a material selected from the group consisting of an oil of lubricating viscosity and a grease; and
   remainder an additive comprising amino di(alkylaryl) phosphorodithioate which is a condensation product of unpolymerized cashew nut shell liquid phosphorodithioic acid with at least one amine.

9. The lubricant as claimed in claim 8, wherein the additive is present in an amount ranging from about 0.1 to about 10 wt %.

10. The lubricant as claimed in claim 8, wherein the additive is present in an amount ranging from 0.5 to 5 wt %.

11. The lubricant as claimed in claim 8, wherein the oil of lubricating viscosity is selected from the group consisting of a mineral oil, a synthetic oil, and mixtures thereof.

12. The lubricant as claimed in claim 8, wherein the material is a grease selected from the group consisting of a lithium grease, a calcium grease, a sodium grease, a clay, and a titanium grease.

13. The lubricant as claimed in claim 8, wherein the additive comprising amino di(alkylaryl)phosphorodithioate is derived from distilled cashew nut shell liquid.

14. The lubricant as claimed in claim 13, wherein the additive is present in an amount ranging from about 0.1 to 10 wt %.

15. The lubricant as claimed in claim 13, wherein the additive is present in an amount ranging from about 0.5 to 5 wt %.

16. The lubricant as claimed in claim 13, wherein the oil of lubricating viscosity is selected from the group consisting of a mineral oil, a synthetic oil, and mixtures thereof.

17. The lubricant as claimed in claim 13, wherein the material is a grease selected from the group consisting of a lithium grease, a calcium grease, a sodium grease, a clay, and a titanium grease.

* * * * *